(12) United States Patent
Parnell et al.

(10) Patent No.: US 6,343,694 B1
(45) Date of Patent: *Feb. 5, 2002

(54) MODULAR MEDICAL EQUIPMENT SYSTEM

(76) Inventors: Tracey Parnell, Suite 107-15499 Casteledowns Road, Edmonton, Alberta (CA), T5X 5X3; Shane Parnell, 238 Sheep River Lane, Okotoks, Alberta (CA), T0L 1T4

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/191,596

(22) Filed: Nov. 13, 1998

(51) Int. Cl.[7] .............................................. B65D 83/10
(52) U.S. Cl. ...................... 206/370; 206/570; 150/110; 190/110; 383/39; 383/41
(58) Field of Search .......................... 206/370, 363–369, 206/570; 383/38, 39, 40, 41, 42; 190/108, 110; 150/110

(56) References Cited

U.S. PATENT DOCUMENTS

| | | | | |
|---|---|---|---|---|
| 657,463 A | * | 9/1900 | Simpson ..................... 206/370 |
| 1,498,455 A | * | 6/1924 | Johnson ..................... 211/126.1 |
| 2,648,366 A | * | 8/1953 | Higbee et al. ............... 206/370 |
| 2,832,389 A | * | 4/1958 | Smith ........................... 383/9 |
| 3,116,773 A | * | 1/1964 | Kikas ........................... 383/22 |
| 3,981,398 A | * | 9/1976 | Boshoff ....................... 206/570 |
| 4,415,089 A | * | 11/1983 | Ruffa .......................... 206/370 |
| 4,513,866 A | | 4/1985 | Thomas |
| 4,773,535 A | * | 9/1988 | Cook ........................... 206/373 |
| 4,901,899 A | * | 2/1990 | Barrett ........................ 224/223 |
| 5,096,030 A | * | 3/1992 | Espinosa et al. ............. 190/108 |
| 5,836,453 A | * | 11/1998 | Herrera ....................... 206/702 |
| 5,848,700 A | * | 12/1998 | Horn ........................... 206/570 |
| 5,865,314 A | * | 2/1999 | Jacober ....................... 206/570 |
| 5,897,209 A | * | 4/1999 | Roegner ...................... 383/39 |
| 5,971,119 A | * | 10/1999 | Chi ............................. 190/108 |
| 5,992,665 A | * | 11/1999 | Deeter ........................ 220/23.4 |
| 6,000,509 A | * | 12/1999 | Chisholm ..................... 190/109 |

FOREIGN PATENT DOCUMENTS

| | | | | |
|---|---|---|---|---|
| DE | 827997 | * | 7/1949 | .................. 206/370 |
| WO | 92/11832 | * | 7/1992 | .................. 206/570 |

* cited by examiner

*Primary Examiner*—David T. Fidei
*Assistant Examiner*—Jila M. Mohandesi
(74) *Attorney, Agent, or Firm*—Anthony J. Casella; Gerald E. Hespos (57) ABSTRACT

The present invention provides for a modular based system for carrying and displaying medical equipment and supplies, incorporating highly organized, procedurally oriented storage modules designed with visible pockets and restraining devices. The modules can function independently or as part of a larger unit that includes many modules. They can be attached to a display board by one of several securement devices, which in turn can be attached to corresponding mobile stands or to a variety of surfaces in a variety of transport media. The modules can also be placed in one or more unique portable bags, vests or backpacks specifically designed to accommodate the modules through its corresponding fastening devices.

4 Claims, 9 Drawing Sheets

MODULAR MEDICAL EQUIPMENT SYSTEM

FIELD OF THE INVENTION

This invention relates to carrying cases for emergency medical supplies and more particularly to modular carrying cases, designed to be highly visible and easily accessible.

BACKGROUND OF THE INVENTION

Critical emergency care is based on the principle of being able to perform life-saving or morbidity reducing procedures with little or no delay. For the critically-ill or severely injured victim, the difference between life and death often depends upon immediate access to emergency medical treatment.

Presently emergency supplies and equipment are organized in bags with pockets or pouches or in tackle-like boxes. They are organized to be conveniently stored, but not conveniently and procedurally accessed. This becomes a great challenge to the care giver when a emergency situation requires the need to search through contents hidden in pouches, pockets or drawers. All too frequently this search proves fruitless as the item was presumed to be in a storage pouch, pocket, or drawer, but was missed in the hurry to re-stock. It can be very difficult, time demanding and inefficient to open and close each storage section and to attempt to remember its contents.

The difficulty is further amplified by situations in which different emergency personnel are present at a scene. Personnel may be unfamiliar with the contents and arrangement of the kit of a different level of care provider (i.e. advanced versus basic life support). Because the contents are either hidden or difficult to see, personnel who are not familiar with a particular kit may have difficulty in locating the medical supplies needed for treating a particular injury. Common emergency equipment is often stored in different locations and standardization is difficult to achieve. Further time delays, complicated by an increase in frustration and misunderstanding among care providers, can add to making a bad situation worse.

Another problem often encountered while treating victims at the scene of an accident is the difficulty in treating more than one patient at a time. Although more than one trained person may be present, there is often only one kit containing emergency medical supplies available. If all the medical supplies are kept within one bag, box or pack and cannot be conveniently and effectively removed for use at another location, the entire kit must be transferred around from patient to patient, creating a highly ineffective care situation.

Furthermore, when attempting to function in an unfamiliar or threatening environment as is encountered in mass casualty, disaster or military settings, it is vital that personnel know the exact location and availability of supplies and be able to accurately monitor and manage the level and volume of resources required. Critical time is lost in attempting to locate, restock and ensure a constant flow of needed supplies. Current kits are unable to be upscaled to deal with mass casualty situations.

Current kits also require complete reworking to be functional as kits for different levels of care, or to function at special event, disaster or hospital medical stations. As well, they are not always particularly suited for adaptation to transport vehicles, air, land or sea.

It would, therefore, be a significant advancement in the provision of care if a system could be designed which would be readily adaptable to a variety of work environments, personnel and situations and which would logically organize necessary equipment and supplies in such a manner that would allow them to be readily visible and immediately accessible.

SUMMARY OF THE INVENTION

The present invention can be understood as a medical supply storage system, incorporating functional modular storage units into an array of advanced modular portable bags, packs, display board panels and vests.

It is an object of the present invention to provide a carrying system for medical supplies that is an improvement over the prior art.

According to one aspect of the present invention, the present invention relates to a device for the storage and handling of equipment and/or supplies, including at least one panel provided with means for securement of such equipment or supplies to said panel, and means integral with said panel for facilitating access to said equipment or supplies.

In another broad aspect, the present invention relates to a carrying and display case for retaining supplies, said case comprising at least one modular unit and a plurality of panels, said panels having an interior and an exterior surface wherein at least one panel is adapted for supporting the modular unit.

In a further broad aspect, the present invention relates to a case for carrying and displaying medical supplies comprising: a plurality of rigid panel means releasably connected together for forming a body and defining an exterior surface and an interior space therein; a plurality of unit carrying means for holding and retaining medical supplies; said unit carrying means having an exterior surface with a first attachment means and said exterior surface of said panels having a second attachment means wherein when said first attachment means engages said second attachment means the unit carrying means is supported on said panels.

The present invention has several advantages. It provides visible, immediate access to equipment and supplies, therefore, improving efficiency in the provision of care. Its modular structure is designed such that the system is readily adapted to use in air, land or water transport. The modular design is versatile in that it enables customization of the modules on the display units, bags, packs or vests according to requirements or individual preferences, while still ensuring standardization. Providers require minimal time to familiarize themselves with where items are located. The use of ready duplicate modules significantly diminishes delays in multiple or mass casualties or when modules are required for urgent transport. The use of fastening devices on the modules, display boards and portable bags to which they can be attached, along with the highly visible, easy accessible modular design of the entire system, allows the individual care provider to tailor the system to their needs by choosing and arranging modules in a variety of storage and display options.

Numerous other advantages, objects and features of the present invention will be readily apparent to those skilled in the art from a review of the following detailed descriptions of the preferred embodiments in conjunction with the accompanying drawings and claims.

BRIEF DESCRIPTION OF THE DRAWINGS

Preferred embodiments of the present invention will now be further described in greater detail and will be better understood when read in conjunction with the accompanying drawings, in which.

DETAILED DESCRIPTION OF THE DRAWINGS

The present invention is a medical supply storage system comprising a series of medical supply storage modules for storing and accessing the supplies necessary for a particular medical procedure or function. These modules can be used and displayed independently or stored as a complete system within a carrying case or pouch.

Figure 1A:
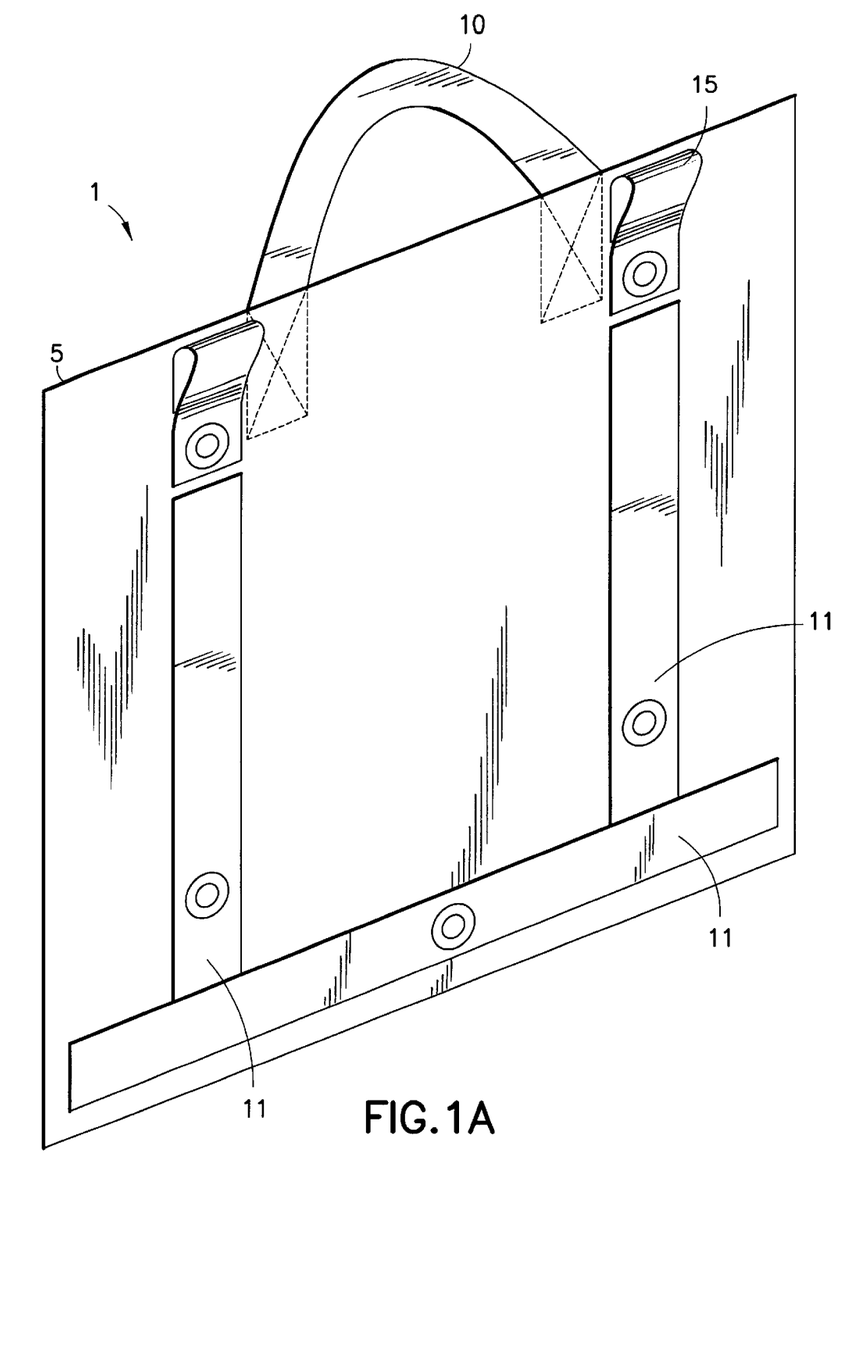
FIGS. 1A and 1B are rear views of a modules of the system.
Figure 1B:
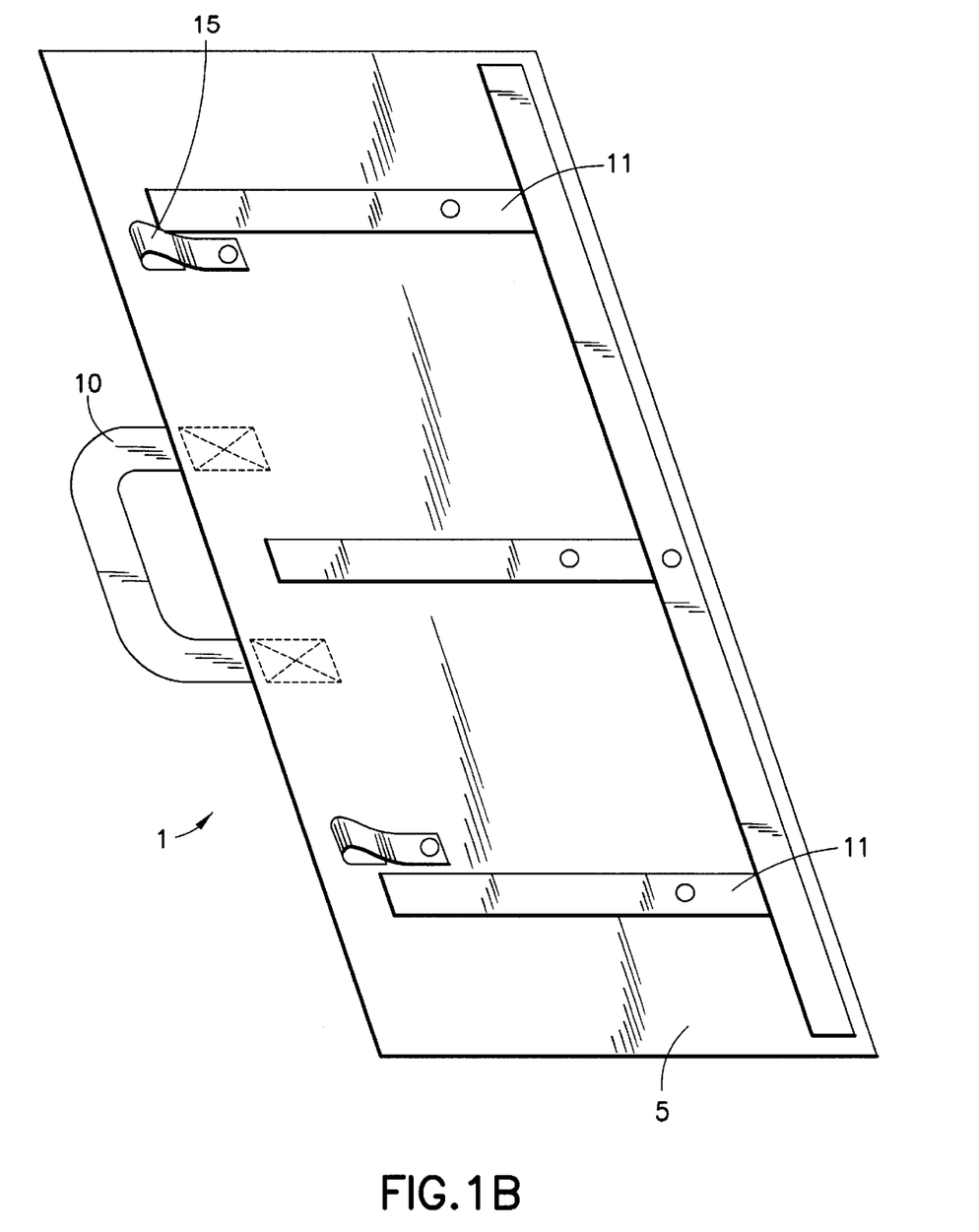
Figure 2A:
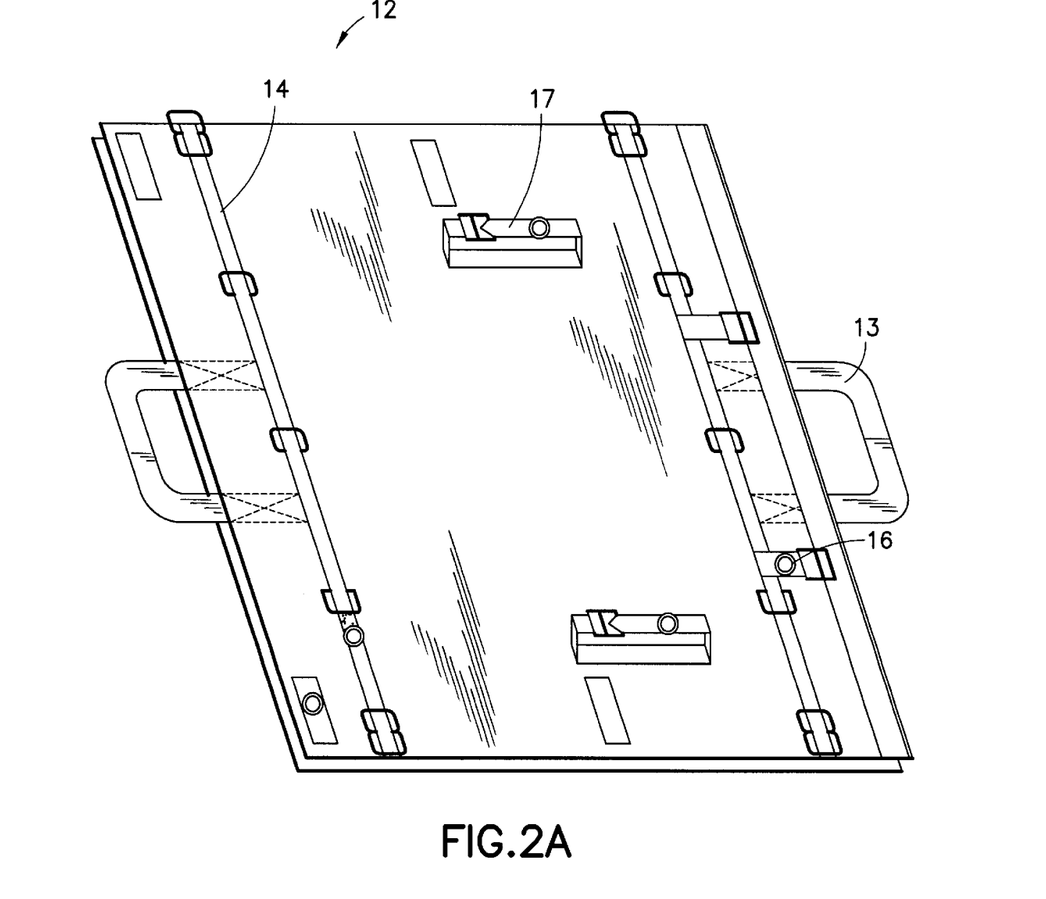
FIGS. 2A and 2B are rear views of display boards upon which the modules of the system can be attached.
Figure 2B:
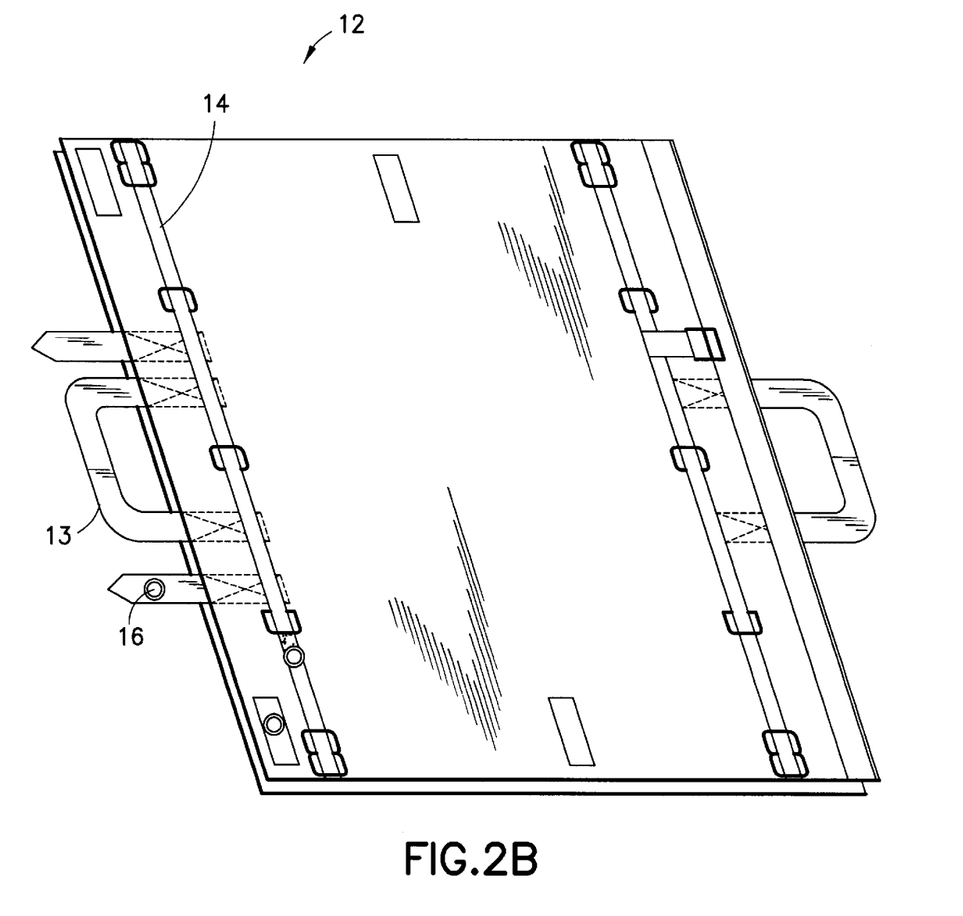
Figure 3A:
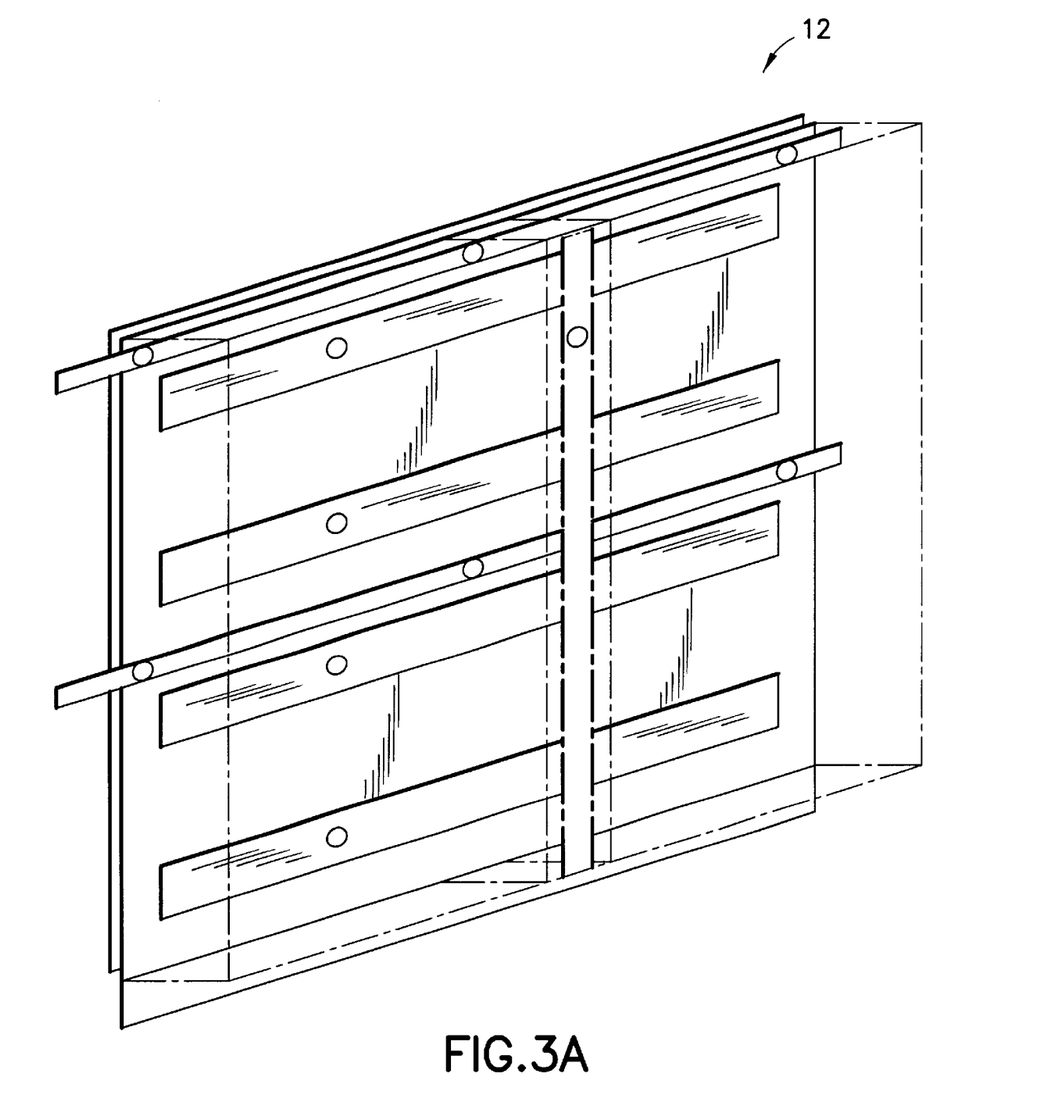
FIGS. 3A and 3B are front views of the display boards shown in FIGS. 2A and 2B.
Figure 3B:
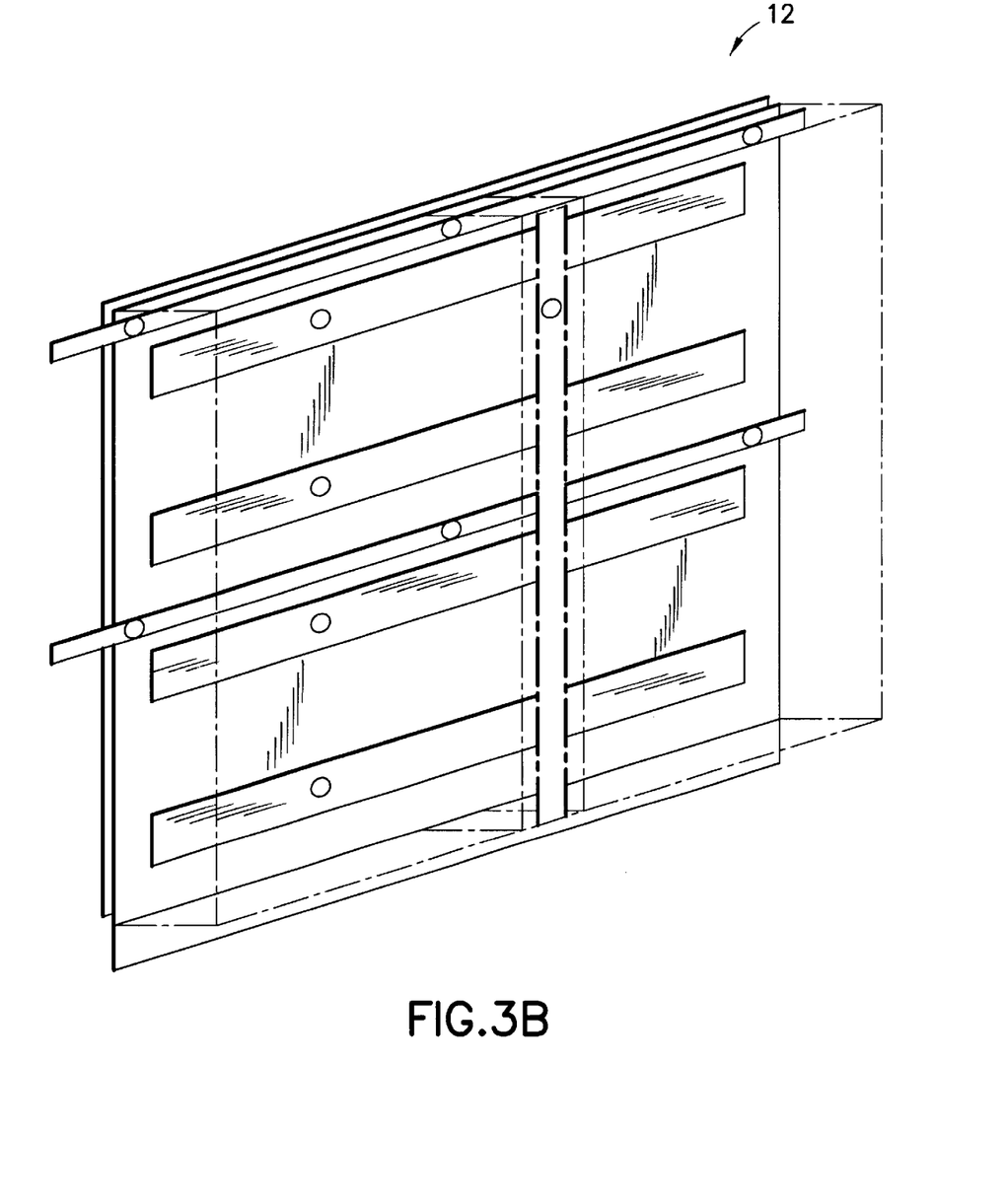

Referring to FIGS. 1A and 1B, the modules 1 are generally rectangular in shape and include a rigid base panel 5 to support the contents of the module 1. The modules 1 are equipped with a carrying handle 10 or a loop attachment such that the module 1 can be individually carried or hung from a pole or structure at the site of use. The modules 1 can be attached to other modules 1 using VELCRO™, strap or other attachment means 11.

The modules 1 can be displayed at a site by attachment to a display board 12 (FIGS. 2A, 2B, 3A and 3B). The display board 12 is generally rectangular in shape and forms a rigid structure for attachment of the modules 1. The display boards 12 are fitted with handles 13 at opposite ends of the board 12 which allow the board 12 and attached modules 1 to be hooked onto a vertical surface such as a wall or the inside or outside of a vehicle.

The display boards 12 are composed of flexible material and can conform to retain modules 1 of various shapes and sizes. The modules 1 are attached to the display board 12 by attachment devices 14. It will be obvious to one skilled in the art that the attachment devices 14 can include various forms of fasteners, straps or clipping means, some or all of which can be used depending on the terrain or situation.

The display boards 12 can be attached to one other (top and bottom) by fastener devices 16 which may take the form of straps or buckles. On the left and right hand side of the display boards 12 there is also a sewn-in dust and debris cover that can be used to cover any modules 1 that are placed on the display boards 12 (not shown) and protect the display boards 12 from unfavourable environmental conditions.

Figure 4A:
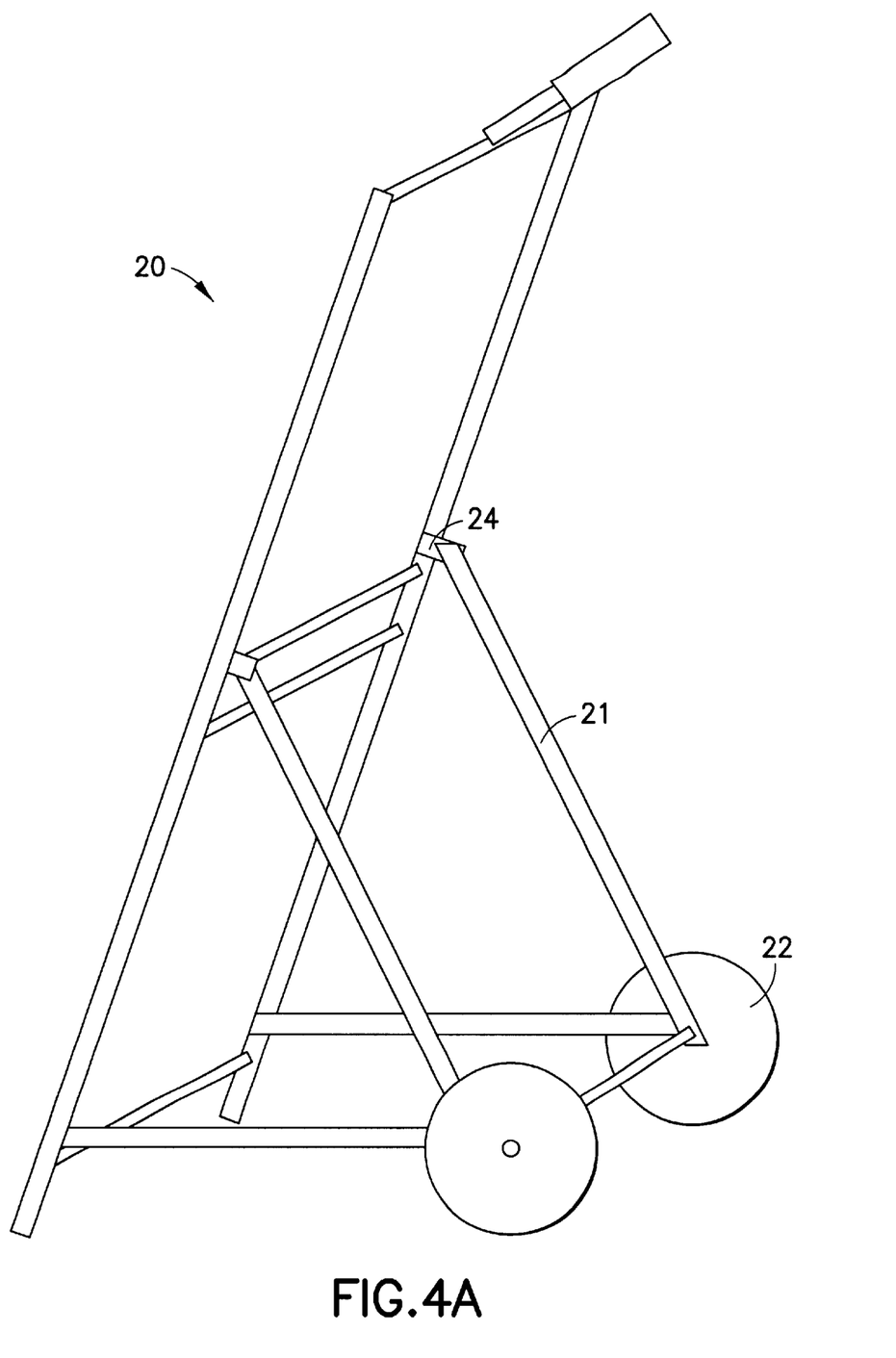
FIGS. 4A and 4B are side views of collapsible metal stands onto which the display boards can be secured.
Figure 4B:
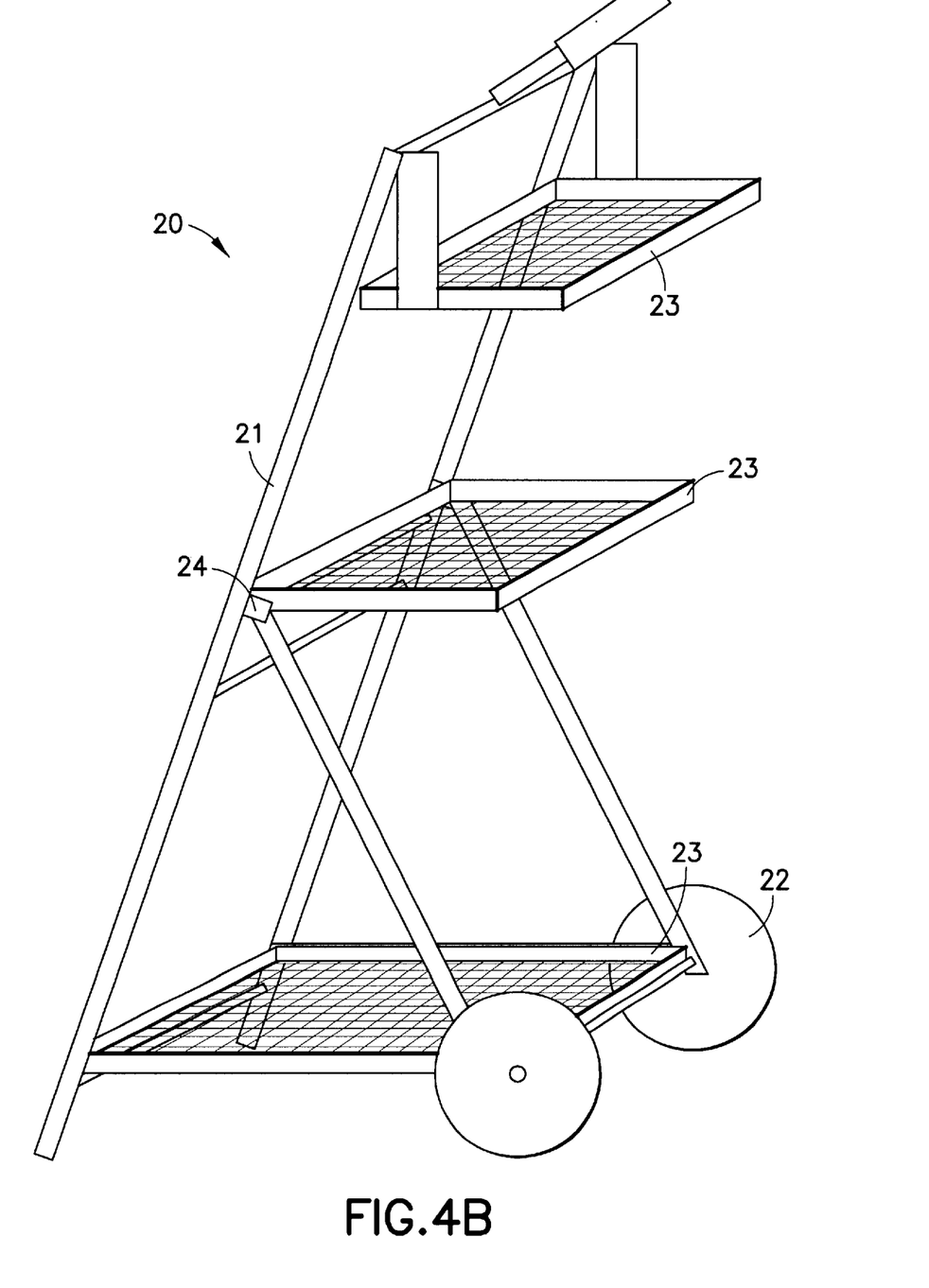

The display boards 12 can be further attached to collapsible stands 20 (FIGS. 4A and 4B) by attachment means 17 including strapping and clip means. The stand 20 is composed of a frame 21, wheels 22, and removable shelving 23 (FIG. 4B) located at high, middle and low levels with respect to the height of the stand 20. The shelving 23 allows for display of a variety of emergency equipment, including oxygen, cardiac monitors and defibrillators. The stand 20 also includes hinge means 24 which provide the stand 20 with the capability of being collapsed at its mid-point, thereby forming a compact horizontal stand or a wall mounted vertical unit.

Figure 5:
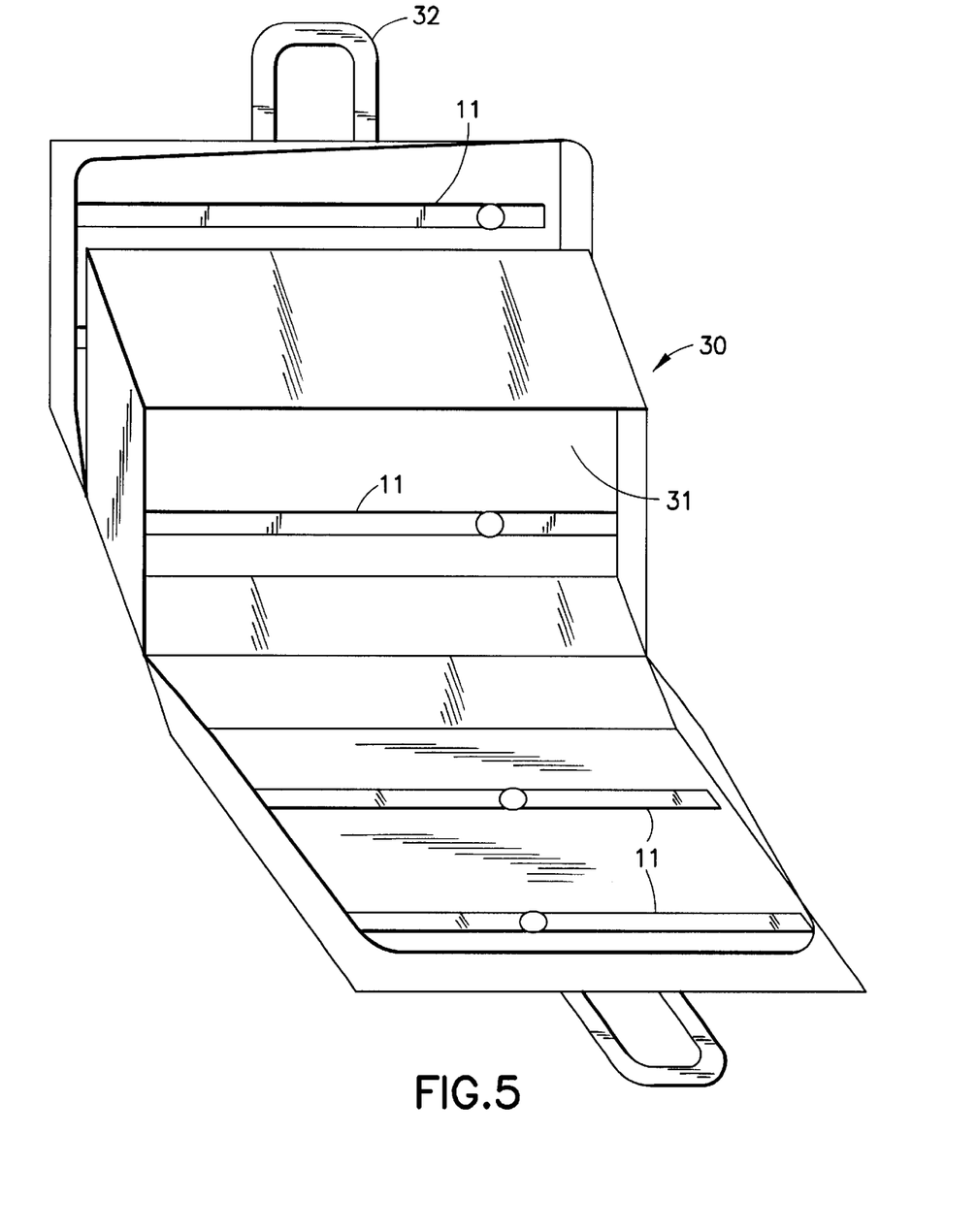
FIG. 5 is a front perspective view of a carrying case used for carrying the modules of the system.

The modules 1 of the medical supply storage system of the present invention can also be stored, transported and facilitated within a carrying case 30 (FIG. 5). The case 30 includes rigid upright units 31 for the storage of medical instruments as well as VELCRO™ 11, strapping and other attaching devices. The case 30 can be carried using handles 32, shoulder straps or backpack attachments. Moreover, the carrying case may be configured as a backpack, a pack for storage in a vessel or vehicle, or as a vest, as will be obvious to one skilled in the art.

It will also be obvious to one skilled in the art that the medical supply storage system of the present invention can be reconfigured to suit individual needs, training levels, and situational demands. It can function as a portable system for use in the field, in the back of any transport vehicle, or as a stand alone workstation in a more stationary area whether it is a military or civilian unit medical station or a tertiary care emergency department. Each case may be stocked with procedural modules having medical supplies appropriate to the training of the emergency personnel using that particular case.

For example, the system may include modules 1 for fluid resuscitation, airway management, intubation, pharmacological interventions, haemorrhage control, assessment tools, surgical thoracic intervention, venous access, emergency amputation and surgical intervention, and immobilization. This list is not exhaustive. Generally, the modules 1 are designed to achieve maximum efficiency according to the procedural supplies retained within the module 1.

While the invention has been described in relation to medical supplies and its use by emergency response personnel, the invention may also be used for other purposes. For example, the case may be used by roadside service mechanics for carrying necessary tools and equipment needed to aid stranded motorists having varying vehicle makes and models. Tools for a particular situation may be kept within each module for easy access. Other uses are within the scope of the invention and the above-described embodiments of the present invention are meant to be illustrative of preferred embodiments of the present invention and are not intended to limit the scope of the present invention.

The embodiments of the invention in which an exclusive property or privilege is claimed are defined as follows:

1. A medical equipment storage system comprising a plurality of substantially rigid panels each having a front surface provided with a first means of securement for securing of medical equipment and supplies thereon and a rear surface provided with a first attachment means, said panels include a second means for securement for securing said panels to an external support;

a pouch having an interior and an access opening to said interior, wherein a surface of the interior of said pouch being provided with a second attachment means complementary to the first attachment means of said panels to permit said panels to be attached to the interior of said pouch; and     a fastening device for securing a plurality of said pouches together.

2. The medical equipment storage system of claim 1, wherein said first means for securement of said medical equipment and supplies to said panel is selected from the group consisting of pockets, straps, buckles, hooks, and loops.

3. The medical equipment storage system of claim 1, wherein said first attachment means comprises a strap on said rear surface of said panel and said second attachment means being a complementary strap, one of said straps being provided with an array of closed loops and the other of said straps being provided with a complimentary array of resilient hooks that are releasably engageable with the loops.

4. The medical equipment storage system of claim 1, wherein said first means for securement of the medical equipment and supplies to said panel comprises securement means for medical supplies for use in procedures selected from the group consisting of fluid resuscitation, airway management, intubation, pharmacological interventions, haemorrhage control, medical assessment, surfacial thoracid intervention, venous access, emergency amputation and surgical intervention, and immobilization.

\* \* \* \* \*